United States Patent [19]

Gillies et al.

[11] Patent Number: 4,663,281

[45] Date of Patent: May 5, 1987

[54] ENHANCED PRODUCTION OF PROTEINACEOUS MATERIALS IN EUCARYOTIC CELLS

[75] Inventors: Stephen D. Gillies, Scituate; Susumu Tonegawa, Chestnut Hill, both of Mass.

[73] Assignee: Mass Institute of Technology, Cambridge, Mass.

[21] Appl. No.: 592,231

[22] Filed: Mar. 22, 1984

[51] Int. Cl.$^4$ .................. C12P 21/00; C12N 5/02; C12N 1/00; C12N 15/00
[52] U.S. Cl. .................. 435/68; 435/241; 435/317; 435/172.3; 935/36; 935/34
[58] Field of Search .................. 435/68, 70, 71, 240, 435/241, 317, 172.1, 172.3; 935/22, 23, 24, 26, 32, 33, 34, 36

[56] References Cited

U.S. PATENT DOCUMENTS

| | | |
|---|---|---|
| 4,349,629 | 9/1982 | Carey et al. .................. 435/172 |
| 4,371,625 | 2/1983 | Tiollais .................. 435/317 |
| 4,374,927 | 2/1983 | Sninsky et al. .................. 435/68 |
| 4,399,216 | 8/1983 | Axel et al. .................. 435/6 |
| 4,405,712 | 9/1983 | Vande Woude et al. .................. 435/5 |
| 4,418,149 | 11/1983 | Ptashne et al. .................. 435/253 |

FOREIGN PATENT DOCUMENTS

| | | |
|---|---|---|
| 0011562 | 5/1980 | European Pat. Off. . |
| 0052002 | 5/1982 | European Pat. Off. . |
| 0064681 | 11/1982 | European Pat. Off. . |
| 0067540 | 12/1982 | European Pat. Off. . |
| 0072925 | 3/1983 | European Pat. Off. . |
| 0076037 | 4/1983 | European Pat. Off. . |
| 0077689 | 4/1983 | European Pat. Off. . |
| WO81/02425 | 9/1981 | PCT Int'l Appl. . |
| WO82/00158 | 1/1982 | PCT Int'l Appl. . |
| WO83/00702 | 3/1983 | PCT Int'l Appl. . |
| 2100738 | 1/1983 | United Kingdom . |
| 2105344 | 3/1983 | United Kingdom . |

OTHER PUBLICATIONS

Laimins et al., P.N.A.S. 79:6453–6457 (Nov.) '82.
Krueger et al., Meth. Enz., vol. 100:501–503, 1983.
P. Bentvelzen, Ann. Rev. Gen. 16:273–279, 1982.
de Villiers et al., Nucl. Ac. Des. 9: 6251–6264, 1981.
de Villiers and Schaffner, "A Small Segment of Polyoma Virus DNA Enhances the Expression of a Cloned B-Globin Gene over a Distance of 1400 Base Pairs," Necleic Acids Research v. 9, No. 23 p. 6251–(1981).
Conrad and Botchan, "Isolation and Characterization of Human DNA Fragments with Nucleotide Sequence Homologies with the Simian Virus 40 Regulatory Region," Molecular and Cellular Biol. v. 2, No. 8 pp. 949–965 (1982).
Weiher et al., "Multiple Point Mutations Affecting the Simian Virus 40 Enhancer," Science v. 219 pp. 626–631 (1983).
Banerji et al. "A Lymphocyte—Specific Cellular Enhancer is Located Downstream of the Joining Region in Immunoglobin Heavy Chain Genes," Cell v. 33 pp. 729–740 (1983).

(List continued on next page.)

Primary Examiner—Thomas G. Wiseman
Assistant Examiner—Thomas D. Mays
Attorney, Agent, or Firm—Lahive & Cockfield

[57] ABSTRACT

Disclosed is a method of enhancing expression of recombinant DNA in eucaryotic cells. A tissue specific enhancer element obtained from the genome of an organism and active in a selected tissue type is combined with a transcriptionally competent transcription unit comprising a promoter and exons encoding for the proteinaceous material of interest (or its precursor). This recombinant DNA is transfected into cells derived from the same tissue as the tissue in which the enhancer element normally functions to enhance expression of endogeneous DNA. The resulting transformants express the exons of the transcription unit at high levels as the enhancer element increases the copy number of mRNA. The enhancer element operates to increase transcription independent of its orientation and position provided it is located within an active region on the DNA, generally between about 1–10 kilobases (kb) from the 3′ or 5′ end of the transcription unit.

25 Claims, 10 Drawing Figures

OTHER PUBLICATIONS

Boss, "Enhancer Elements in Immunoglobulin Genes," Nature v. 303 pp. 281–282 (1983).

Gillies et al., "A Tissue—Specific Transcription Enhancer Element is Located in the Major Intron of a Rearranged Immunoglobin Heavy Chain Gene," Cell v. 33 pp. 717–728 (1983).

Marx, "Immunoglobulin Genes Have Enhancers," Science v. 221 pp. 735–737 (1983).

Banerji et al. "Expression of a B–Globin Gene is Enhanced by Remore SV40 DNA Sequences" Cell v. 27 pp. 299–308 (1981).

Moreau et al. "The SV40 72 Base Repair Repeat has a Striking Effect on Gene Expression both in SV40 and Other Chimeric Recombinants," Nucleic Acids Research v. 9, No. 22 p. 6047–(1981).

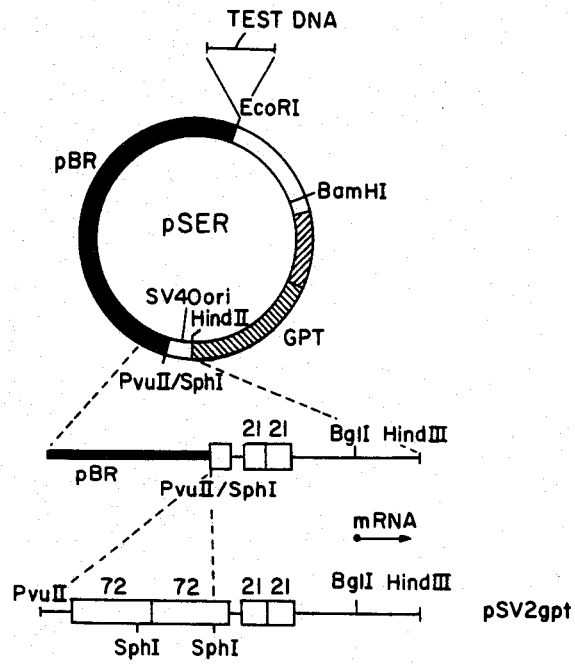

FIG. 9

```
Xba I
                                                50                                        100
TCTAGAGAGG TCTGGTGGAG CCTGCAAAAG TCCAGCTTTC AAAGGAACAC AGAAGTATGT GTATGGAATA TTAGAAGATG TTGCTTTTAC TCTTAAGTTG
                                                150                                       200
GTTCCTAGGA AAAATAGTTA AATACTGTGA CTTTAAAATG TGAGAGGGTT TTCAAGTACJ CATTTTTTTA AATGTCCAAA ATTTTTGTCA ATCAATTTGA
                                     Δ2 ┌250                                              300
GGTCTTGTTT GTGTAGAACT GACATTACTT AAAGTTTAAC CGAGGAATGG GAGTGAGGCT CTCTCATACC CTATCCAGAA CTGACTTTTA ACAATAATAA
                                  Hinf I 350                                   Pvu II     400
ATTAAGTTTA AAATATTTTT AAATGAATTG AGCAATGTTG AGTTGAGTCA AGATGGCCGA TCAGAACCAG AACACCTGCA GCAGCTGGCA GGAAGCAGGT
                                                450                                       500
CATGTGGCAA GGCTATTTGG GGAAGGGAAA ATAAAACCAC TAGGTAAACT TGTAGCTGTG GTTTGAAGAA GTGGTTTTGA AACACTCTGT CCAGCCCCAC
               Dde I                           550          Hinf I                        600
CAAACCGAAA GTCCAGGCTG AGCAAAACAC CACCTGGGTA ATTTGCATTT CTAAAATAAG TTGAGGATTC AGCCGAAACT GGAGAGGTCC TCTTTTAACT
                                    Δ1 ┌650                                    EcoRI     700
TATTGAGTTC AACCTTTTAA TTTTAGCTTG AGTAGTTCTA GTTTCCCCAA ACTTAAGTTT ATCGACTTCT AAAATGTATT TAGAATTCAT TTTCAAAATT
              ┐Δ2                               750                                       800
AGGTTATGTA AGAAATTGAA GGACTTTAGT GTCTTTAATT TCTAATATAT TTAGAAAACT TCTTAAAATT ACTCTATTAT CTTCCCTCT GATTATTGGT
                 ┐Δ1                            850                                       900
CTCCATTCAA TTATTTTCCA ATACCCGAAG TCTTTACAGT GACTTTGTTC ATGATCTTTT TTAGTTGTTT GTTTTGCCTT ACTATTAAGA CTTTGACATT
                  Dde I  950                                                     Xba I
CTGGTCAAAA CGGCTTCACA AATCTTTTTC AAGACCACTT TCTGAGTATT CATTTTAGGA GAAATATTTT TTTTTTAAAT GAATGCAATT ATCTAGA
```

FIG. 10

ENHANCED PRODUCTION OF PROTEINACEOUS MATERIALS IN EUCARYOTIC CELLS

BACKGROUND OF THE INVENTION

The U.S. government has rights in this invention by virtue of Grant No. NIH-5-R01-AI17879-02 of the National Institute of Health.

This invention relates to methods of efficiently expressing DNA introduced into eucaryotic cells. More specifically, the invention relates to a method of exploiting the genetic mechanism of certain types of eucaryotic cells to produce relatively large quantities of a protein of interest or its precursor.

The protein production of most animal cells is limited to synthesis of enzymes used by the cell for metabolism and to structural proteins, surface proteins, and numerous proteinaceous materials having specialized functions such as interferons, lymphokines, and hormones. Typically, such cells produce relatively modest amounts of these proteins. Other types of cells in addition are capable of producing and secreting large amounts of proteinaceous material for systemic use in the animal body. Examples of the latter type of cells include cells of the circulatory system which produce globulins and fibrinogen, liver cells which produce serum albumin, and the beta cells of Islets of Langerhans which produce insulin. If the genetic mechanisms responsible for the high level production could be used to produce lymphokines, interferons, antibodies, or other proteinaceous materials of interest, large supplies of valuable proteins could be made available.

Hybridoma technology in effect harnesses the proteinproducing capabilities of a B cell to produce monoclonal antibodies and accordingly achieves this goal to some extent. To produce hybridomas, a lymphoid cell that has been stimulated to produce antibody by in vivo or in vitro immunization is fused with an immortal cell line, for example, a myeloma cell line. The fusion products are grown in a selective medium in which the parental myeloma cannot survive and then screened for a clone which secretes the monoclonal antibody of interest. Using this technique, one may obtain monoclonal antibodies of high affinity for specific antigens. However, no reproducible method has been developed which permits application of the hybridoma technology to the production of non-immunoglobulin proteins. Furthermore, certain types of potentially useful hybridoma cells, e.g., human x human hybridomas, are notoriously difficult to culture.

De Villiers et. al., in Nucleic Acid Research, Volume 9 No. 23, pg. 6251, 1981, disclose work involving the linking of a rabbit hemoglobin gene with a 244 base pair DNA fragment derived from the beginning of the polyoma virus late region. After transfection of such recombinant DNA into mouse 3T6 and human Hela cells, the polyoma sequences were found to strongly enhance the level of correct beta globin gene transcripts over a distance of at least 1400 base pairs. The authors hypothesized that this 244 base pair DNA fragment of viral origin, termed an "enhancer", might be useful as a component of mammalian expression vectors. Conrad et. al., in Molecular and Cellular Biology, pages 949–965, August, 1982, disclose that a recombinant library of human DNA sequences was screened with a segment of simian virus 40 DNA that spans the viral origin of replication. One SV40 hybridized fragment contained a sequence which increased the efficiency of thymidine kinase transformation in human cells by approximately 20-fold. The authors reported that this effect was orientation independent when the sequence was present at the 3' end of the chicken thymidine kinase gene and proposed that this segment of DNA contains a sequence analogous to the 72 bp repeats of SV40. However, no direct evidence was presented indicating this element is a transcription enhancer. For example, the activity seen by these authors could result from increased integration of the introduced thymidine kinase gene into the host DNA. Weiher et. al., in Science, Volume 219, page 626, Feb. 11, 1983, disclose that viral enhancers can stimulate transcription from heterologous promoters and that such enhancers have been found in papovaviruses and retroviruses, e.g., SV-40, polyoma, Moloney sarcoma and Bovine papilloma.

SUMMARY OF THE INVENTION

It has now been discovered that eucaryotic cells which produce large amounts of protein, e.g., immunoglobulin, do so because of an enhancer element present in the natural genome of the protein producing cell in association with the transcription unit encoding the protein. The enhancer element in such cells operates by greatly increasing the transcription rate of the expressed DNA resulting in high mRNA copy numbers. Operability of the eucaryotic transcription enhancers is substantially independent of the orientation of the enhancer element and substantially independent of its position with respect to the transcription unit, provided the enhancer element is located within an "active region" which may span a region up-stream or down-stream of the transcription unit of 1000–10,000 base pairs or more. The cellular transcription enhancers appear to be tissue specific but species nonspecific. They have core sequences in common with viral enhancers.

The invention exploits these discoveries to provide a process for producing a proteinaceous material of interest and transformants which may be cultured to produce such materials. In accordance with the invention, either exogenous or endogenous proteins may be produced, i.e., either proteins not encoded in the natural genome of the host cells, or proteins which are encoded but are not normally expressed by the host cells, or are expressed only at low levels. Broadly, an enhancer element is identified as hereinafter disclosed and excised from the genome of a eucaryotic cell, e.g., an animal cell, and then ligated with DNA comprising a transcriptionally competent transcription unit including one or more exons encoding for the proteinaceous material of interest (or its precursor). The resulting recombinant DNA is transfected into a cell line derived from the same tissue type as the cell in which the enhancer is active, and preferably from the same cell type as the cell in which the enhancer is active. Preferably, the recombinant DNA comprising the tissue specific enhancer element ligated to the transcription unit is incorporated into a vector such as a plasmid or a virus which is introduced into the cell line by conventional techniques. Certain of the resulting successful transformants can produce the proteinanceous material of interest (or its precursor) encoded by the transcription unit at levels substantially equal to or approaching the level of expression of the endogenous transcription unit normally associated with the enhancer. Generally, best results are achieved when the transfection results in a stably transformed cell, i.e., one in which the recombinant DNA is integrated into the chromosomal DNA of the cell line or is stably maintained in an extrachromasomal state. Preferred enhancer elements for use in the invention are those which, when present in the endogenous genome of a cell, function to enhance production of a proteinaceous material produced in large quantities, e.g. albumin, globulins, fibrinogen, or hormones.

Novel vectors of the invention for use in transfecting eucaryotic cells derived from a selected tissue comprise a recombinant DNA which includes a transcription unit encoding the proteinaceous material of interest, e.g., a cDNA, and an associated promoter sequence, and another DNA segment containing the enhancer element. Vectors of the invention also include those comprising a restriction site and an enhancer element located sufficiently close to the restriction site so that a transcription unit inserted into the site is expressed at enhanced levels when the recombinant vector is transfected into a cell line derived from the same cell or tissue type in which the enhancer is active. Such "universal vectors" may also include a promoter, e.g., an inducible promoter, upstream of the restriction site. The enhancer, if located at a site within an active region on the recombinant DNA sufficiently close to the transcription unit, enhances production of mRNA. The enhancer element used in the vector must be operative in a cell from the same tissue type as the cell to be transformed. It is operative to enhance production of the mRNA independent of its orientation and position within the active region.

The novel eucaryotic cell transformants for producing proteinanceous material comprise a cell from a selected tissue, modified by transfection with recombinant DNA comprising the transcription unit and an enhancer element endogenous to and active in the selected tissue.

By following the teachings disclosed herein, one can select a mitotically competent cell line, e.g., a myeloma, hepatoma, or other continuous cell line available from various repositories and/or researchers in recombinant DNA technology, and can transfect the cell line with recombinant DNA including an appropriately positioned enhancer and a transcription unit for the protein of interest. If the selected enhancer normally functions to increase transcription, thereby enabling the cell to produce large quantities of a proteinaceous substance, a temporarily or stably transformed cell line can result which exhibits enhanced transcription of mRNA and efficiently produces valuable proteinaceous products.

Practice of the invention enables the genetic engineer to exploit the prolific protein production ability of certain cells to produce large amounts of a protein of interest in a viable, stable cell culture.

Accordingly it is an object of the invention to provide a generalized method of engineering eucaryotic cells to produce large quantities of proteins. Another object is to provide a novel family of vectors for transfecting eucaryotic cells to produce cultures of transformants having improved protein producing properties. These and other objects and features of the invention will be apparent from the following description and from the drawing.

BRIEF DESCRIPTION OF THE DRAWINGS

FIG. 9 is a restriction map of plasmid pSER illustrating the differences between it and its parent plasmid pSV2 gpt. Note that the segment of SV-40 DNA containing the viral enhancer element (72 bp repeat) has been deleted to produce plasmid pSER. The gpt resistant phenotype cannot be expressed in cells after transfection with plasmid pSER unless a DNA restriction fragment (test DNA), which is capable of functioning as an enhancer in the cell, is inserted in the EcoRI or other suitable site on plasmid pSER. This plasmid can thus be used to screen cellular DNA for enhancer elements. The solid bar represents sequences derived from plasmid pBR322; thin striped bar sections represent sequences derived from SV-40; wide striped bar sections represent gpt coding sequences; and FIG. 10 is an illustration of the nucleotide sequences of DNA comprising an enhancer element located on a major intron of a γ2b heavy chain murine gene (X$_{2/3}$ fragment).

DESCRIPTION

Figure 1:
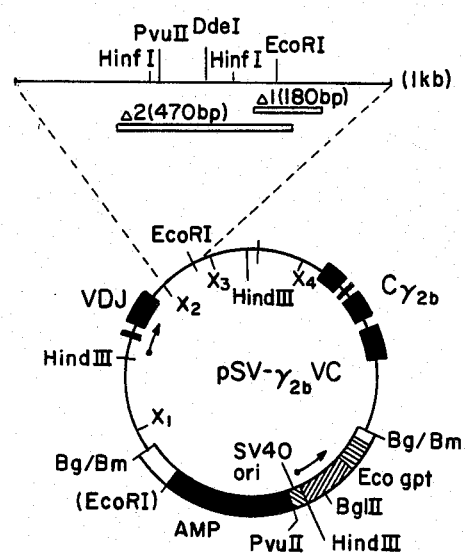
FIG. 1 is a partial restriction map of Plasmid pSV-$\gamma$2bVC. A 9kb Bgl II fragment was inserted into the Bam HI site (indicated by Bg/Bm) of plasmid pSV2gpt. The Ecogpt gene (wide stripes) is flanked by SV40 sequences (thin stripes) including the origin (ori) of replication and mRNA start site (arrow). The $\gamma$2b gene (narrow line) contains VDJ and C$\gamma$2b exons (solid boxes) and a mRNA start site (arrow) about 30 bp upstream of the VDJ coding sequence. The DNA segments deleted in plasmids pSV-$\gamma$2b3'R$\Delta$1 and pSV-$\gamma$2b3'R$\Delta$2 are shown in linear form above the circular map. The sizes of the deletions, as determined by restriction analysis, are indicated.

Methods of identifying and isolating genes encoding proteins of interest, or for constructing such genes, are now well understood and developed. The literature describes numerous methods useful in obtaining genes encoding various interferons, hormones, antibodies, lymphokines, blood clotting factors, enzymes and many other proteins or glycoproteins useful in medical or veterinary science. This invention provides methods of inducing high level expression of such genes in stable, mitotically competent eucaryotic cell cultures.

The concept of the invention is to exploit tissue-type specific or cell-type specific cell enhancers to produce large quantities of valuable proteins in engineered, continuous cell lines. Any cellular enhancer may be recombined with any gene and any suitable promoter for the gene to achieve these results provided the resultant recombinant DNA is transfected into a cell derived from the same tissue type or the same cell type as the cell in which the enhancer is normally active. Thus, the practice of the invention enables expression of a desired DNA encoding a protein of interest at substantially the same high levels as the natural expression of an endogenous gene in cells capable of producing large quantities of protein such as immunoglobulin, fibrinogen, albumin, or hormones.

Useful enhancer elements may be obtained from a genetic library of human, other animal, or other species, or from a cell sample. The enhancer element will typically be found in association with a transcription unit encoding a protein which is produced in abundance in a particular cell type. Thus, the conventional methods used to locate genes encoding particular materials in natural genomes will be useful in locating functional cellular enhancers. Useful enhancer sequences may be located either upstream, downstream, or within a transcription unit. The enhancer sequences function to greatly increase transcription, but only in a specific tissue-type or cell-type; the enhancer function of the sequences is greatly diminished or totally absent in other types of cells. The enhancer sequences are characterized by substantial insensitivity to changes in orientation and position relative to the transcription unit, provided they are located within an "active region". The active region may span a length of the DNA 10 thousand or more base pairs upstream and downstream from the transcription unit.

DNA comprising the enhancer element is ligated to DNA comprising a transcriptionally competent transcription unit. The unit consists of exons encoding the protein of interest, a promoter, and other regulatory sequences. The enhancer is operative whether located upstream or downstream from the transcription unit or in an intron, provided it is within the active region. However, the level of enhancement may vary somewhat depending on its position relative to the transcription unit. Any suitable promoter may be used, including inducible promoters, e.g., the metallothionein promoters.

This recombinant DNA is then transfected into a cell line which is preferably an established, easily-maintained, and easily grown animal cell line which does not secrete large amounts of protein. The cell line and the enhancer element are selected to be as compatible as possible. Since each of the cell enhancers useful in the invention are tissue-type or cell-type specific, they typically do not function, or function only at very low or undetectable levels when transfected into cell lines derived from tissues different from the tissue in which they are normally active. In some cases, the enhancers are cell-type specific and will not function if placed in a different cell-type, even one derived from the same tissue type.

Accordingly, for optimum results the cell line and the enhancer should be matched as closely as possible. For example, an enhancer operative in B lymphocytes or in a hybridoma to increase production of immunoglobulin should be transfected into a lymphoid cell line, preferably an immortal, B lymphocyte-derived cell line, and most preferably into such a cell line which has lost its ability to express endogenous immunoglobulin. An enhancer which normally functions in a liver cell to increase production of albumin should be used in an immortal cell line of hepatic origin, and preferably a cell line derived from a cell which secretes albumin. In these and other situations the resulting transformants can express protein encoded by the recombinant transcription unit at levels approaching the expression of the endogenous protein.

SELECTION OF ENHANCER

Enhancers active in particular types of eucaryotic cells are present in association with transcription units encoding the various proteins produced by the cells. However, since the entire genome of an individual is present in all of the cells of the individual, enhancers may be derived from any cell of the individual or from a genetic library. Investigation of a number of such cellular enhancers has shown that they have core sequences in common with viral enhancers. Fragments containing enhancer activity which are reduced in size with restriction enzymes lose their enhancer function progressively. Intact enhancer element sequences are often a thousand or more base pairs in length, but residual enhancer activity can often be found in significantly shorter fragments.

A useful approach to identifying and isolating an enhancer useful in a selected cell type, e.g., a lymphoid cell, is to identify the gene for a protein produced in abundance by a lymphoid cell line and to subclone restriction fragments of the gene and its flanking regions into a vector at a location reasonably close to some expressable DNA. The recombinant vectors are then transfected into cells of the selected cell type (here lymphoid cells), and the cells are assayed to determine which if any are producing the protein encoded by the expressable DNA at enhanced levels. Any such recombinant containing the enhancer element may be used as a source of enhancer element for constructing vectors useful in the practice of the invention.

A preferred screening method involves construction of a "test vector". Such a vector imparts a phenotypic characteristic, e.g., resistance to a cell toxin, necessary for cell survival in a screening medium only if, before transfection, an enhancer active in the cell has been recombined in the vector. Such vectors can be constructed by deleting from a known vector the viral enhancer sequences normally associated with expression of the phenotype such that the deletion vector is no longer effective to impart the phenotype. Restriction fragments of the test gene and its flanking region suspected to contain an enhancer are then inserted into the deletion vector, the recombinants are transfected into the cell line, and the cells are cultured in the presence of the toxin. In this circumstance, only clones containing recombinants which include an enhancer element operative in the cell line will survive. This results in a cell culture of cells which must have the phenotype and accordingly must have an enhancer effective in the cells.

The enhancer is then excised from these recombinant vectors and recombined with a transcription unit encoding a protein of interest in the same or a different vector. Vectors including an enhancer element may be constructed using conventional techniques. They may be constructed from phages, animal or other viruses, or plasmids using conventional restriction enzymes, ligases, and other methodology. Vectors and transfection procedures resulting in stably transform cells are preferred. The vectors comprise a DNA segment containing the enhancer function ligated to a DNA segment including a transcription unit, i.e., one or more exons and a promoter.

Transfection of the vector into the eucaryotic cell line can result in transformants which produce protein encoded by the transcription unit at levels comparable to the production of the endogenous protein naturally occurring in cells. The vectors may be introduced into cells by conventional techniques, e.g., employing protoplast fusion, agents such as calcium phosphate, or microinjection.

The invention will be further understood from the following nonlimiting examples, for which all of the starting materials are readily available to those skilled in the art from commercial or other sources.

EXAMPLE 1

Enhanced Expression of Mouse γ2b Heavy Chain Gene in Mouse Myeloma

An immunoglobulin heavy chain gene fragment approximately 9kb long from a phage clone (M141 - p 21) derived from MOPC-141 mouse tumor cells (Sakano et al., Nature, 286, 676–683, 1980) of lymphoid origin, known to be expressed at low levels in transfected mouse L cells, was subcloned into plasmid pSV2 gpt (Mulligan et al., Science, 209, 1422–1427, 1980). This plasmid contains an expressable DNA segment which permits cell growth in the presence of mycophenolic acid when exogeneous xanthine is added to the culture medium.

The recombinant plasmid pSV-γ2bVC was constructed by inserting a 9 kb Bgl II fragment from phage clone M141-p21 into the unique Bam HI site of plasmid pSV2gpt(RI). This latter plasmid was constructed by mutating the Eco RI site of plasmid pSV2gpt. The transcription orientation of the γ2b gene is opposite that of the gpt gene (see FIG. 1).

Plasmid pSVγ2bVC was transfected into the mouse myeloma line J558L, which has lost its ability to express its endogenous heavy chain gene (see Oi et. al., Proc. Nat. Acad. Sci. U.S.A. 80, 825–829). The J558L cells were grown in Dulbecco's modified Eagle's medium (MEM) containing 10% fetal calf serum. J558L cells were transfected by a modification of the protoplast fusion technique (Sandri-Goldin et. al., Mol. Cell. Biol. 1, 743, 752, 1981). Approximately $2 \times 10^6$ cells (grown to a density of 4 to $6 \times 10^5$ cells/ml) were washed once with serum-free MEM, collected by centrifugation (5 min. at 500xg), and suspended by gentle pipetting in the protoplast suspension (approximately $2 \times 10^9$ protoplasts in 4 ml). The cell-protoplast suspension was transferred to a 60 mm dish and centrifuged at 1500 g for 7 min. After gentle aspiration of the supernatant, 1.5 ml of 50% polyethylene glycol (PEG-1500, in serum-free MEM and prewarmed to 37° C.) was added and the dish was spun at 500xg until 90 sec had elapsed from the time of PEG addition. Cells were resuspended by gently pipetting in two 5 ml washes of prewarmed, serum-free MEM which were added to 15 ml of MEM in a 50 ml centrifuge tube. Following centrifugation at 500xg for 5 min, cells were resuspended in growth medium containing kanamycin (100μg/ml) and plated in 96-well dishes at two densities: $1 \times 10^4$ cells per well and $2 \times 10^3$ cells per well. After 48 hr selective medium containing mycophenolic acid (Oi et. al., supra, 1983) was added so that only successfully transfected cells survived.

Figure 2:
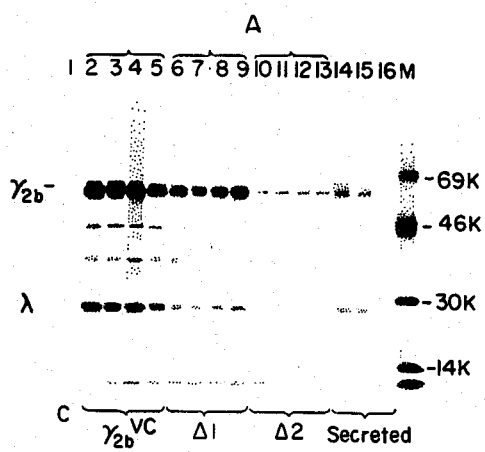
FIG. 2 is an autoradiogram demonstrating the expression of $\gamma$2b heavy chain protein in transfected cells. Transfected cell lines were labeled with $^{35}$S-methionine and cell extracts were analyzed. Immunoprecipitated proteins were analyzed by SDS-polyacrylamide gel electrophoresis and fluorography. Four transfected lines (pools of individual clones) were analyzed for each plasmid tested. Lane 1: control J558L cells; lanes 2-5: cells transfected with plasmid pSV-$\gamma$2bVC; lanes 6-9: cells transfected with plasmid pSV-$\gamma$2b3'R$\Delta$1; lanes 10-13: cells transfected with plasmid pSV-$\gamma$2b3'R$\Delta$2. Secreted proteins from cells transfected with plasmid pSV-$\gamma$2bVC (lane 14), plasmid pSV-$\gamma$2b3'R$\Delta$1 (lane 15), and plasmid pSV-$\gamma$2b3'R$\Delta$2 (lane 16) were immunoprecipitated and analyzed on the same gel.

Cell lines obtained by transfected with plasmid pSVγ2bVC and selection for gpt expression (grown in the presence of mycophenolic acid) were found to express high levels of γ2b heavy chain (FIG. 2, lanes 2–5). These levels of expression of the exogenous γ2b genes are estimated to be about 20% of that of the endogenous γ2b gene in MOPC 141. Apparently, this heavy chain can form an immunoglobulin molecule with the λ light chain of myeloma J558L, because the light chain was immunoprecipitated from cell extracts with antiheavy chain antisera and equimolar amounts of heavy and light chain were secreted into the culture medium (FIG. 2, lane 14).

Deletion mutants of the parental plasmid were constructed to test whether the removal of specific noncoding DNA sequences would affect the expression of the γ2b gene in J558L cells. Because deletions between the VDJ and Cμ exons of an Abelson murine leukemia virus-transformed cell line have been correlated with decreased heavy chain production (Alt et. al., Nature, 296, 325–331, 1982), mutant plasmids were constructed with deletions in this region. Two such plasmids, pSV-γ2b3'RΔ1 and pSVγ2b3'RΔ2 contain overlapping deletions around the unique Eco RI site of the parental plasmid pSV-γ2bVC (FIG. 1 and FIG. 10).

Plasmids pSVγ2b3'RΔ1 and pSVγ2b3'RΔ2 were constructed by digesting Eco RI-cut pSVγ2bVC DNA with exonuclease Bal 31 (1 U/μg of DNA) at 23° C. for 2 or 4 min and recirculizing the products with T4

DNA ligase. The extent of the deletions were determined by restriction analysis and DNA sequencing. These three plasmids were introduced into J558L myeloma cells and the expression of the γ2b heavy chain gene in stably transformed cells was compared.

Figure 3:
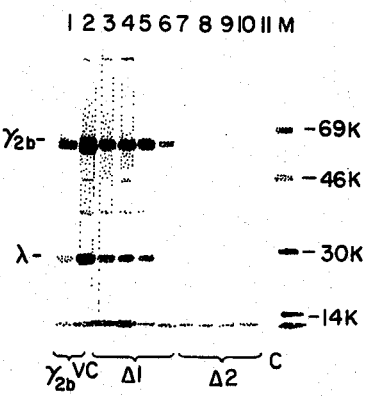
FIG. 3 is an autoradiogram similar to FIG. 2 demonstrating the expression of $\gamma$2b heavy chain protein in subclones of the cell pools used to obtain the results of FIG. 2. Cell lines subcloned from the transfected cell lines were tested for $\gamma$2b heavy chain protein synthesis as in FIG. 1. The plasmids used for transfection are indicated below the autoradiogram. Control (C) cell extract is shown in lane 11. The positions of the $\gamma$2b heavy chain and $\lambda$ light chain (synthesized in J558L cells but not immunoprecipitated in the absence of $\gamma$2b heavy chain) are indicated.

Cell lines obtained by transfection (as set forth above) with plasmid pSV-γ2b3'RΔ1 synthesized high levels (no less than half of the wild type level) of γ2b heavy chain (FIG. 2, lanes 6-9) and secreted immunoglobulin (FIG. 2, lane 15). In contrast, four cell lines obtained by transfection with plasmid pSV-γ2b3'RΔ2 synthesized only low levels (about 5% of the wild type level) of heavy chain (FIG. 2, lanes 10-13). The same results were obtained when subclones of each pool were tested for γ2b heavy chain expression (FIG. 3), although more variation was observed in the level of expression between individual clones. Nonetheless, these results demonstrate that DNA sequences deleted in plasmid pSV-γ2b3'RΔ2, but still present in pSV-γ2b3'RΔ1, (see FIG. 10) are essential for the high level expression of heavy chain genes in myeloma cells.

Figure 4:
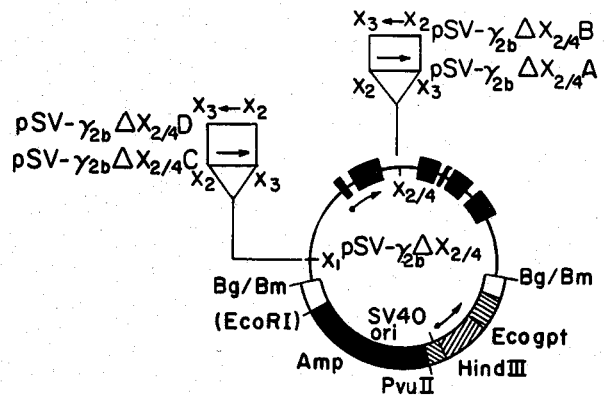
FIG. 4 is a restriction map of plasmid pSV-$\gamma$2b$\Delta$X$_{2/4}$. This plasmid was constructed from plasmid pSV-$\gamma$2bVC (shown in FIG. 1) by removing two Xba I fragments from the $\gamma$2b gene intron (from the X$_2$ to the X$_4$ sites in FIG. 1). Derivatives of plasmid pSV-$\gamma$2b$\Delta$X$_{2/4}$, labeled A through D, contain inserts of the 1 kb X$_{2/3}$ fragment in the sites indicated and the orientation (relative to transcription) is shown with an arrow.

The DNA sequences defined as viral enhancer elements have been shown to stimulate the transcription of homologous or heterologous promoters either upstream or downstream, and in either orientation with respect to the direction of transcription. In order to test whether the putative enhancer sequences located in the major intron of the γ2b gene and present in the pSV-γ2b3'RΔ1 deletion plasmids behave similarly, a plasmid with most of the intron sequences deleted was constructed. A 1 kb Xba I fragment ($X_{2/3}$, see nucleotide sequence, FIG. 10) containing those intron sequences with potential enhancer activity were then inserted into either of two sites and in either of the two orientations. The first corresponds to the original position of this fragment in the parental plasmid (as part of the VDJ-C γ2b intron) and the second is approximately 1.4 kb upstream (on the 5' side of the V gene segment). Four plasmids were obtained which contained the $X_{2/3}$ fragment in the normal or reversed orientation, either upstream or downstream of the mRNA start site (see FIG. 4).

Plasmid pSV-γ2bΔ$X_{2/4}$ was constructed by first digesting plasmid pSV γ2bVC DNA with Bgl II and then partially digesting with Xba I. The 6.5 kb partial digestion product extending from the unique Bgl II site to the Xba I site ($X_2$) on the 3' side of the VDJ exon (clockwise on the map in FIG. 1) and the 5.1 kb complete digestion product extending from the Bgl II site, counterclockwise to the Xba I site ($X_4$) on the 5' side of the C γ2b coding region, were gel purified and ligated. Derivatives of this plasmid (A-D of FIG. 4) were constructed by partially digesting with Xba I, treating the DNA with calf intestine alkaline phosphatase, purifying linear full-length DNA, and ligating the products with the 1 kb Xba I fragment extending from the $X_2$ to $X_3$ sites ($X_{2/3}$ fragment in FIG. 1). The site of insertion and the orientation of the $X_{2/3}$ fragment were determined by restriction analysis.

Figure 5:
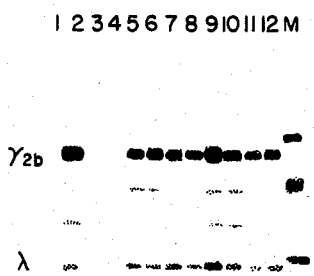
FIG. 5 is an autoradiogram demonstrating the effect of the presence of an enhancer and its orientation and position in expression of $\gamma$2b heavy chain in cells transfected with the plasmids of FIG. 4. Analysis was carried out as described in FIG. 2. Cell lines tested were J558L (lane 1), and those transfected with plasmid pSV-$\gamma$2bVC (lane 2), plasmid pSV2-$\gamma$2b$\Delta$X$_{2/4}$ (lanes 3 and 4), plasmid pSV-$\gamma$2b$\Delta$X$_{2/4}$A (lanes 5 and 6), plasmid pSV-$\gamma$2b$\Delta$X$_{2/4}$B (lanes 7 and 8), plasmid pSV-$\gamma$2b$\Delta$X$_{2/4}$C, (lanes 9 and 10), and plasmid pSV-$\gamma$2b$\Delta$X$_{2/4}$D (lanes 11 and 12)

Cell lines obtained by transfection with the plasmids just described were analyzed for the expression of γ2b heavy chain. As indicated in FIG. 5, cells transfected with plasmid pSV-γ2bΔ$X_{2/4}$ (with most of the intron deleted) did not synthesize significant levels of γ2b protein (lanes 3 and 4). The insertion of the $X_{2/3}$ fragment containing the enhancer into the intron site (the normal position of this fragment) restored the expression of γ2b protein in both the normal (FIG. 5, lanes 5 and 6) or reversed (FIG. 5, lanes 7 and 8) orientations. Similarly, insertion of the same frament upstream of the V gene segment (on the 5' side of the transcriptional promoter) in either the normal (FIG. 5, lanes 9 and 10) or the reversed (FIG. 5, lanes 11 and 12) orientation also restored the expression of γ2b protein to normal levels.

These results clearly demonstrate that the intron sequences deleted in the 3'RΔ2 mutant plasmid have a direct effect on transcription in a manner that is analogous to the viral enhancers. They also show that the enhancer function does not require the expression of these sequences in the γ2b gene primary transcript, because movement of the $X_{2/3}$ fragment outside of the transcription unit (i.e., the $X_1$ site) had no effect on its enhancer activity.

The steady-state level of γ2b mRNA in transfected cell lines was analyzed by Northern gel blotting and hybridization with the C γ2b probe. It should be noted that the γ2b heavy chain gene used in this example does not contain the exons coding for the membrane form of γ2b and thus the only species of mRNA expected in transfected cells is the secreted form (1.7 kb).

Cell lines transfected with plasmid pSV-γ2b VC and plasmid pSVγ2b3'RΔ1 contain high levels of the secreted form of γ2b mRNA. The cell lines transfected with plasmid pSVγ2b3'RΔ2 contained much lower levels of γ2b mRNA of the correct size, in agreement with the decreased level of γ2b heavy chain protein. Thus, mammalian enhancers function at the level of transcription, significantly increasing the copy number of mRNA. In this experiment, the apparent enhancement of protein production was 20 fold. However, in a separate experiment (see below) it was determined that the enhancer element also increased expression of the gpt gene. This separate enhancement resulted in viable transformants containing the enhancer having a plasmid copy number only 5% that of viable transformants containing no enhancer element. Thus, protein expression was actually enhanced about 400 fold on a per gene copy basis.

EXAMPLE II

Enhanced Expression of gpt Gene in Mouse Myeloma

DNA from J558 cells transfected with pSV-γ2b VC, pSVγ2b3'RΔ1, and pSVγ2b3'RΔ2 were analyzed by Southern gel blotting to determine the plasmid copy number and its possible effect on the level of γ2b mRNA. When a pSV2gpt plasmid DNA probe was used for hybridization, a striking difference in plasmid copy number was found. Two prominent bands, corresponding to the two large Hind III fragments (6.2 kb and 5.0 kb) common to all the plasmids, are detected with this probe. The DNA sequences deleted in plasmid pSV-γ2b3'RΔ2 (those required for the high level expression of γ2b mRNA) also have a dramatic effect on the number of copies of plasmid required for transformation to the gpt+ phenotype. When these sequences are present, as they are in plasmids pSV-γ2bVC and pSV-γ2b3'RΔ1, a low copy number is sufficient for gpt transformation. In the absence of these sequences, as in pSV-γ2b3'RΔ2, the copy number is increased at least 20-fold, presumably to compensate for a comparable decrease in gpt mRNA transcription.

The DNA sequences required for the high level expression of γ2b mRNA therefore also enhance the level of expression from the heterologous SV40 promoter at least 20 times.

EXAMPLE III

Cellular Enhancer Genes are Tissue Specific

The γ2b gene used in examples I is also accurately transcribed in mouse fibroblasts (Ltk⁻ cells) cotransfected with the herpes virus tk gene (thymidine kinase) and plasmid ppLγ2b VC. The level of γ2b gene expression in these cells was found to be proportional to the number of transfected genes, but is at least two orders of magnitude less per gene copy than in the myeloma cells used in the previous examples. Thus it appeared likely that the enhancer element, described above, does not function in nonlymphoid cells.

Figure 6:
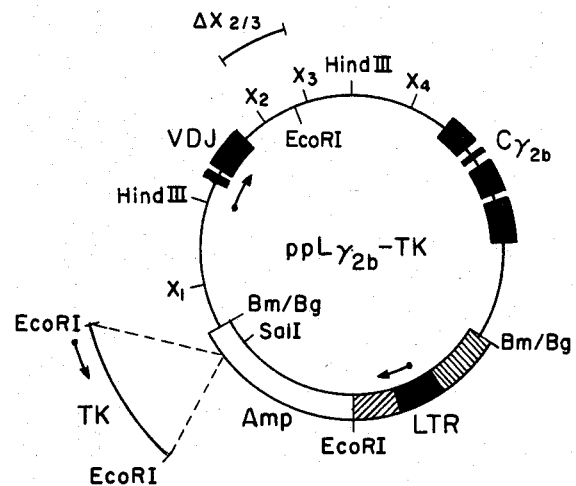
FIG. 6 is a restriction map of plasmids ppL 2b-tk and ppL$\gamma$2b$\Delta$X$_{2/3}$-tk. Plasmid ppL $\gamma$2b-tk was constructed by inserting a 2.3 kb fragment of the herpes virus tk gene into the unique Sal I site of plasmid ppL-$\gamma$2bVC. The direction of transcription of the tk gene (arrow) is opposite that of the $\gamma$2b gene. The sequences deleted in plasmid ppL-$\gamma$2b$\Delta$X$_{2/3}$-tk are indicated.

In order to compare the levels of γ2b gene expression in fibroblasts, with and without the immunoglobulin enhancer, a deletion mutant, ppL γ2bΔX$_{2/3}$, lacking these sequences was constructed (FIG. 6). The plasmids were then modified so that a high copy number of γ2b genes would be integrated into the transfected L cells and increase the expression of the γ2b gene to an easily detectable level. This was done by inserting a truncated tk gene (a 2.3 kb Eco RI fragment containing only limited 5' upstream sequences) into both the wild type and mutant plasmids. Transformation to the tk+ phenotype with this fragment requires the transfer of multiple plasmid copies into cells, thus another gene on the same plasmid would also be present at a high copy number in tk transformants.

Figure 7:
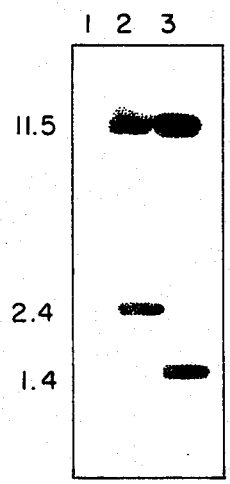
FIG. 7 is an autoradiogram illustrating the results of Southern gel blotting analysis of DNA from L tk- cells (lane 1), and cells transfected with plasmid ppL-$\gamma$2b-tk (lane 2), or plasmid ppL-$\gamma$2b$\Delta$X$_{2/3}$-tk (lane 3). DNA was digested with Hind III and hybridized to nick-translated $\gamma$2b DNA (the 9 kb Bgl II fragment used for plasmid construction)

Plasmids ppL γ2b tk and ppLγ2bΔX$_{2/3}$ tk were introduced into mouse Ltk⁻ cells and the tk+ transformants (approximately 50 individual clones) were pooled, grown in mass culture, and tested for the presence of γ2b DNA sequences. As seen in FIG. 7, each transfected cell line contained comparable numbers of tandem, head-to-tail oligomers of either plasmid. Control experiments (not shown) indicate that individually cloned cell lines also contain the same number (about 15 copies per cell) of transfected plasmid DNA. Apparently the copy number is determined by the level of expression of the tk gene which, in this case, has been reduced considerably by the deletion of the upstream sequences. To compensate for the low level of expression, multiple copies of the tk gene are required for tk transformation. This, then, is analogous to the results with pSV2gpt vectors described in Example II.

Figure 8:
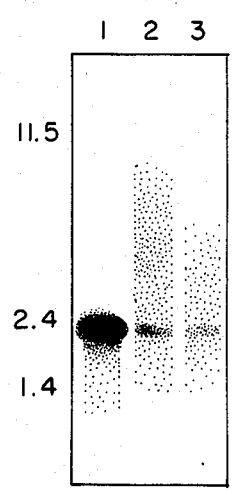
FIG. 8 illustrates the results of Northern gel blotting analysis of total cell RNA from MOPC 141 myeloma cells (lane 1), and mouse L cells cells transfected with plasmid ppLγ2b-tk (lane 2), or plasmid ppLγ2bΔX$_{2/3}$-tk (lane 3). Nick-translated Cγ2b probe was used for hybridization.

Comparing the expression of the normal and mutant γ2b heavy chain genes in these cell lines by Northern gel blotting analysis of total cell RNA, as seen in FIG. 8, the steady-state level of γ2b mRNA is not affected by the deletion of the immunoglbulin enhancer. It was concluded that the low level expression of the heavy chain gene in L cells is a result of the fact that this enhancer element is functional only in lymphoid cells. Additional experiments carried out to test the tissue specificity of the immunoglobulin enhancer confirm this conclusion.

EXAMPLE IV

Isolation of Enhancer Elements From Animal Cell Genomes

A plasmid vector suitable for screening animal DNA restriction fragments for enhancer activity was constructed by digesting pSV2gpt DNA with Sph I and Pvu II and removing the 3' protruding bases with T4 DNA polymerase (O'Farrell, Bethesda Research Labs Focus 3(3), 1, 1981). Ligation of the blunt ends produced a modified vector, designated pSER (see FIG. 9), which no longer included the SV40 enhancer. Plasmid pSV2gpt, when transfected into either the J558L myeloma or a B lymphoma line A20-2J, could transform the cells to the gpt+ phenotype whereas pSER could not. Thus, pSER is dependent on the addition of enhancer sequences for efficient transformation. By transfecting pSER constructs comprising inserted putative enhancer sequences, fragments containing enhancer activity may be isolated.

For example, to test the possibility that an enhancer element might be associated with the mouse E$_\beta$ gene, restriction fragments of the gene and its flanking regions were subcloned into the EcoRI site of plasmid pSER, and the ability of the recombinant plasmids to transform the B lymphoma line, A20-2J, to the gpt+ phenotype was analyzed.

Only one region out of 28 kb of E$_\beta$ coding and flanking sequences was found to be positive in this assay—a 4.1 kb Hind III-EcoRI fragment containing the first E$_\beta$ exon and approximately 2.7 kb of upstream sequence. The site of insertion of this fragment in plasmid pSER was 2.5 kb away from the SV40 promoter, and the 4.1 kb fragment worked equally well in both orientations. Furthermore, the fragment could be substituted for the deleted SV40 enhancer. It was therefore concluded that an enhancer element was located in this region of the E$_\beta$ gene.

The fragments tested for enhancing activity in the pSER assay included three which extend from the 5' end of the 4.1 kb fragment (Hind III site) but differ at their 3' ends. Fragments extending either to the BstXI site near the E gene promoter (HX fragment) or to the Bam HI site at about −600 (HB fragment) contain full enhancing activity. The BstXI to EcoRI fragment (XR), containing the first E$_\beta$ gene exon and a portion of the first intron, had no detectable enhancer activity. Two short sequences upstream of the promoter had been identified as conserved elements when compared to the murine E$_\alpha$ and human DR$_\alpha$5' flanking regions. Since the HB and HX fragments worked equally well in the enhancer assay, even though these sequences were not contained in the HB fragment, it was concluded that these elements are not necessary for enhancing activity.

Subfragments of the 2.0 kb HB fragment were negative in the pSER assay. These included the fragments produced by cleavage with PvuII (HP and PB) and a fragment spanning the PvuII site. Thus, most of the sequences contained in the 2.0 kb HB fragment are required for enhancing activity.

Next the recombinant plasmids that exhibited enhancer activity in A20-2J cells were tested for enhancing activity in other murine cell types. No enhancer activity was detected when the 4.1 kb or HB fragment recombinants were used to transfect fibroblasts (L cells), indicating that this enhancing activity is also tissue-specific. These same plasmid constructs were also negative in a myeloma cell line (J558L), a lymphoid-derived (Ia-negative) cell type which represents the next step of differentiation after the Ia-positive B cell. In contrast, the pSER recombinant containing the immunoglobulin heavy-chain (IgH) enhancer described above was found to be positive in both the B lymphoma (A20-2J) and myeloma lines. This result is not unexpected since both cell types express their functionally rearranged IgH genes.

In order to show that the enhancement of transformation frequencies is correlated with enhancement of transcription, the HB fragment from the E$_\beta$ gene was inserted into plasmid pSV-γ2bΔX$_{2/4}$ and the levels of γ2b mRNA in stably transformed A20-2J or J558L cells was analyzed. The levels of γ2b mRNA, determined by SI nuclease protection, were compared in A20-2J and J558L cells transfected with plasmid pSV-γ2bΔX$_{2/4}$ containing either no inserted DNA, fragment X$_{2/3}$ (IgH enhancer), or the E$_\beta$ HB fragment in either orientation. The results show that J558L cells transfected with the construct containing the IgH enhancer contained high levels of γ2b mRNA. No γ2b mRNA could be detected in J558L cells transfected with the constructs containing the E$_\beta$ HB fragment in either orientation even with much longer exposures of the autoradiogram. Lower levels of γ2b mRNA were detected in A20-2J cells transfected with the plasmid construct containing the IgH enhancer fragment. In contrast to the results with J558L cells, A20-2J cells transfected with the E$_\beta$ HB fragment constructs contained levels of γ2b mRNA that were comparable to that seen with the IgH enhancer. These results are in agreement with the data obtained from the pSER transformation assay and confirm that the IgH sequences function as an enhancer in both cell types while the E$_\beta$ HB fragment functions as an enhancer in a more specific manner—only in the Ia-postive B lymphoma but not in another lymphoid-derived cell type.

The invention may be embodied in other specific forms without departing from the spirit and scope thereof. Other embodiments are within the claims which follow.

What is claimed is:

1. A process for producing a proteinaceous material in a mammalian cell line derived from a selected tissue type comprising the steps of:
    combining DNA comprising a mammalian a tissue specific cellular enhancer element with DNA comprising a transcription unit encoding said proteinaceous material or a precursor thereof to produce transcriptionally competent recombinant DNA, said tissue specific cellular enhancer element, when present in the endogenous genome of a cell from said selected tissue type, being operable naturally to increase the production of an endogenous proteinaceous substance;
    transfecting cells of said mammalian cell line with said recombinant DNA; and
    culturing said transfected cell line to produce enhanced quantities of said proteinaceous material.

2. The process of claim 1 wherein said enhancer element, when present in the endogenous genome of a cell from said selected tissue type, functions to enhance production of a proteinaceous substance selected from the group consisting of albumin, globulins, fibrinogen, and hormones.

3. The process of claim 1 wherein said combining step includes combining said recombinant DNA with a vector selected from the group consisting of plasmids and viruses.

4. The process of claim 3 wherein said vector further includes expressable DNA which corresponds to a gene coding for a selectable marker.

5. The process of claim 1 wherein said transfecting and culturing steps result in a stably transformed cell line.

6. The process of claim 1 wherein said enhancer element, when present in the endogenous genome of a lymphoid cell, functions to enhance expression of DNA encoding a globulin.

7. The process of claim 1 wherein said enhancer element comprises at least a portion of the nucleotide sequences set forth in FIG. 10 and said cell line is a lymphoid cell line.

8. The process of claim 1 wherein said cell line is a myeloma cell line and said enhancer element, when present in the endogenous genome of a lymphoid cell, enhances the production of an immunoglobulin.

9. The process of claim 1 wherein the cell line transfected with said recombinant DNA is derived from the same cell type as the cell in which said enhancer element is active.

10. A vector for transfecting a mammalian cell derived from a selected tissue type to produce a cell line which secretes a proteinaceous material, said vector comprising an exon encoding said proteinaceous material or a precursor thereof and a promoter sequence, and recombined therewith, tissue specific mammalian cellular enhancer element at a site within an active region of said vector sufficiently close to said transcription unit to enhance production of mRNA independent of its orientation and position within said active region, said tissue specific cellular enhancer element, when present in the endogenous genome of a cell from said selected tissue type, being operable naturally to increase production of an endogenous proteinaceous substance.

11. The vector of claim 10 wherein said enhancer element, when present in the endogenous genome of a cell from said selected tissue type, functions to enhance the production of a proteinaceous substance selected from the group consisting of albumin, globulins, fibrinogen, and hormones.

12. The vector of claim 10 further comprising expressable DNA which corresponds to a gene coding for a selectable marker.

13. The vector of claim 10 comprising a member selected from the group consisting of plasmids and viruses.

14. The vector of claim 10 wherein said enhancer element and said transcription unit are derived from different cell lines.

15. The vector of claim 10 wherein said enhancer element, when present in the endogenous genome of a lymphoid cell, is operative naturally to enhance production of immunoglobulin.

16. The vector of claim 10 wherein said enhancer element, when present as part of the endogenous genome of a lymophoid cell in an intron of a γ2b heavy chain gene, serves to enhance production of a γ2b heavy chain protein.

17. The vector of claim 10 wherein said enhancer element comprises at least a portion of the nucleotide sequences set forth in FIG. 10.

18. A mammalian cell transformant for producing a proteinaceous material, said transformant comprising a genetically modified cell derived from a selected mammalian tissue type containing a transfected DNA comprising:
    a transcription unit comprising an exon encoding said proteinaceous material or a precursor thereof and a promoter sequence; and, recombined therewith,
    tissue specific a mammalian cellular enhancer element at a site within an active region of said DNA sufficiently close to said transcription unit to enhance production of mRNA independent of orientation and position within said active region, said tissue specific cellular enhancer element, when present in the endogenous genome of a cell from said selected tissue type, being operative naturally to enhance production of an endogenous proteinaceous substance.

19. The transformant of claim 18 wherein said enhancer element, when present in the endogenous genome of a cell from said selected tissue type, functions to enhance the production of a proteinaceous substance selected from the group consisting of albumin, globulins, fibrinogen, and hormones.

20. The transformant of claim 18 wherein said genetically modified cell is a lymphoid cell and said enhancer element, when present in the endogenous genome of a lymphoid cell, enhances the production of an immunoglobulin.

21. The transformant of claim 18 comprising a stably transformed cell.

22. The transformant of claim 20 wherein said enhancer element comprises at least a portion of the nucleotide sequences set forth in FIG. 10.

23. The transformant of claim 18 comprising a genetically modified cell.

24. A vector for receiving DNA encoding a proteinaceous material and for transfecting a mammalian cell derived from a selected tissue type to produce a cell line which produces said proteinaceous material, said vector comprising a restriction site for receiving a gene encoding said proteinaceous material and tissue specific a mammalian cellular enhancer element located within an active region of said vector sufficiently close to said restriction site to enhance production of mRNA corresponding to a gene inserted into said restriction site, said tissue specific cellular enhancer element, when present in the endogenous genome of a cell from said selected tissue type, being operable naturally to increase production of an endogenous proteinaceous substance.

25. The vector of claim 27 further comprising a promoter upstream of said restriction site.

* * * * *